United States Patent
Tirtowidjojo et al.

(10) Patent No.: US 11,358,918 B2
(45) Date of Patent: Jun. 14, 2022

(54) METHOD FOR THE PRODUCTION OF A HALOGENATED ALKENE BY CATALYZED DEHYDROHALOGENATION OF A HALOGENATED ALKANE

(71) Applicant: Blue Cube IP LLC, Clayton, MO (US)

(72) Inventors: Max Tirtowidjojo, Clayton, MO (US); Manfred Kokott, Clayton, MO (US); Marc Sell, Clayton, MO (US); John D. Myers, Clayton, MO (US); Anja Peters, Clayton, MO (US)

(73) Assignee: Blue Cube IP LLC, Clayton, MO (US)

( * ) Notice: Subject to any disclaimer, the term of this patent is extended or adjusted under 35 U.S.C. 154(b) by 0 days.

(21) Appl. No.: 16/981,984

(22) PCT Filed: Apr. 2, 2019

(86) PCT No.: PCT/US2019/025336
§ 371 (c)(1),
(2) Date: Sep. 17, 2020

(87) PCT Pub. No.: WO2019/195250
PCT Pub. Date: Oct. 10, 2019

(65) Prior Publication Data
US 2021/0002191 A1    Jan. 7, 2021

Related U.S. Application Data

(60) Provisional application No. 62/652,097, filed on Apr. 3, 2018.

(51) Int. Cl.
C07C 17/357    (2006.01)

(52) U.S. Cl.
CPC .................. *C07C 17/357* (2013.01)

(58) Field of Classification Search
CPC ........ C07C 17/395; C07C 21/04; C07C 17/38; C07C 17/25; C07C 17/383
See application file for complete search history.

(56) References Cited

U.S. PATENT DOCUMENTS

| 2014/0206911 | A1 | 7/2014 | Sherwood |
| 2014/0221705 | A1 | 8/2014 | Wang et al. |
| 2014/0275659 | A1 | 9/2014 | Yang et al. |
| 2015/0274616 | A1 | 10/2015 | Yang et al. |
| 2016/0107960 | A1* | 4/2016 | Ondrus ................. C07C 17/395 570/189 |

FOREIGN PATENT DOCUMENTS

WO    2015175791    11/2015

OTHER PUBLICATIONS

International Search Report dated Jun. 13, 2019 for PCT/US2019/025336.
Written Opinion of the International Searching Authority dated Jun. 13, 2019 for PCT/US2019/025336.

* cited by examiner

*Primary Examiner* — Jafar F Parsa
(74) *Attorney, Agent, or Firm* — Polsinelli PC

(57) ABSTRACT

The present invention provides methods for the preparation of halogenated alkenes from halogenated alkanes using a homogeneous catalyst.

20 Claims, 2 Drawing Sheets

METHOD FOR THE PRODUCTION OF A HALOGENATED ALKENE BY CATALYZED DEHYDROHALOGENATION OF A HALOGENATED ALKANE

CROSS-REFERENCE TO RELATED APPLICATIONS

This application is a national stage entry of US2019/025336 filed Apr. 2, 2019, which claims the benefit of U.S. Provisional application 62/652,097 filed Apr. 3, 2018, each of said applications are expressly incorporated herein by reference in their entirety.

FIELD OF THE INVENTION

The present disclosure generally relates to a process for preparing halogenated alkenes from halogenated alkanes using a dehydrochlorination process.

BACKGROUND OF THE INVENTION

Chlorinated alkenes are useful intermediates for many products including agricultural products, pharmaceuticals, cleaning solvents, gums, silicones, and refrigerants.

A method for producing a chlorinated alkene comprises contacting the chlorinated alkane with an aqueous base in a dehydrochlorination process. Generally, these processes are efficient, yet they require a co-solvent such as an alcohol to provide miscibility of the organic and aqueous phases. Processes that do not utilize a co-solvent have been developed, but they are inefficient and require additional separation steps, which reduces the yield of the chlorinated alkene. Additionally, the by-product from the dehydrochlorination processes, aqueous sodium chloride is generally purged from the process, causing increased amounts of waste for the process.

An improvement to the base dehydrochlorination process described above utilizes a small amount of a phase transfer catalyst. The phase transfer catalyst provides miscibility of the organic and aqueous phases and enhances the kinetics of the process. Due to the cost of the phase transfer catalyst, the overall cost for producing a chlorinated alkene on a production scale by adding a phase transfer catalyst is increased. At the completion of the process, the phase transfer catalyst is normally purged to waste.

Methods have been developed utilizing Lewis acids to dehydrochlorinate a chlorinated alkane. Kokai JP 1974-66613 teaches and discloses a process for the production of 1,1,3-trichloropropene from 1,1,1,3-tetrachloropropane utilizing 0.1-0.3 wt % of $FeCl_3$ in solid form at a temperature of 80° 0-95° C. The $FeCl_3$ must be thoroughly mixed with the chlorinated alkane to ensure proper kinetic of the process. In U.S. Pat. No. 8,877,991, a process is disclosed for the production of 1,1,3-trichloropropene from 1,1,1,3-tetrachloropropane. This patent teaches and discloses utilizes 0.08 wt % of $FeCl_3$, with added water up to 0.4 wt % at a temperature of 120° C. This patent further discloses that added water improves the selectivity of the process yet reduces the conversion to about 30%. U.S. Pat. No. 8,889,927 teaches and discloses a process for the preparation of 1,1,3-trichloropropene and/or 3,3,3-trichloropropene. This patent teaches and discloses utilizing 0.03-0.11 wt % of $FeCl_3$, 0.001-5.0 wt % of tetrachloropentane isomers, at a temperature of the process ranging from 50°-140° C. where the weight % (wt %) of the trichloropropene isomers range from 40 to 70 wt % with high selectivity.

It would be desirable to develop a process for preparing halogenated alkenes utilizing a small amount of catalyst, preparing the halogenated alkene in high selectivity, producing the halogenated alkene in high yield, and allowing for easy separation and recycling of materials in the process.

SUMMARY OF THE INVENTION

Provided herein are processes for preparing and isolating a halogenated alkene via a dehydrohalogenation reaction of halogenated alkane. The process comprises a) preparing an anhydrous liquid reaction mixture in a reactor wherein the reaction mixture comprises a halogenated alkane, a homogeneous catalyst, and optionally a solvent; b) heating the reaction mixture to form the halogenated alkene, light by-products, and heavy by-products; c) separating the halogenated alkene from the contents of the reaction mixture; and d) disposing of the heavy by-products.

In another aspect, disclosed herein are processes for the preparation and isolation of 1,1,3-trichloropropene, 3,3,3-trichloropropene, and combinations thereof via a dehydrochlorination reaction of 1,1,1,3-tetrachloropropane. The process comprises a) preparing an anhydrous liquid reaction mixture in a reactor wherein the reaction mixture comprises 1,1,1,3-tetrachloropropane, a homogeneous catalyst, and optionally a solvent; b) heating the reaction mixture to form the halogenated alkene, light by-products, and heavy by-products; c) separating the halogenated alkene from the contents of the reaction mixture; and d) disposing of the heavy by-products.

In another aspect, disclosed herein are processes for the preparation and isolation of 1,1,2,3-tetrachloropropene, 2,3,3,3-tetrachloropropene, and combinations thereof via a dehydrochlorination reaction of 1,1,1,2,3-pentachloropropane. The process comprises a) preparing an anhydrous liquid reaction mixture in a reactor wherein the reaction mixture comprises 1,1,1,2,3-pentachloropropane, a homogeneous catalyst, and optionally a solvent; b) heating the reaction mixture to form the halogenated alkene, light by-products, and heavy by-products; c) separating the halogenated alkene from the contents of the reaction mixture; and d) disposing of the heavy by-products.

In another aspect, disclosed herein are processes for the preparation and isolation of 1,1,3,3-tetrachloropropene, 1,3,3,3-tetrachloropropene, and combinations thereof via a dehydrochlorination reaction of 1,1,1,3,3-pentachloropropane. The process comprises a) preparing an anhydrous liquid reaction mixture in a reactor wherein the reaction mixture comprises 1,1,1,3,3-pentachloropropane, a homogeneous catalyst, and optionally a solvent; b) heating the reaction mixture to form the halogenated alkene, light by-products, and heavy by-products; c) separating the halogenated alkene from the contents of the reaction mixture; and d) disposing of the heavy by-products Other features and iterations of the invention are described in more detail below.

BRIEF DESCRIPTION OF FIGURES

The present patent or application file contains at least one drawing executed in color. Copies of this patent or patent application publication with color drawing(s) will be provided by the Office upon request and payment of the necessary fee.

The following figures illustrate non-limiting embodiments of the present invention.

DETAILED DESCRIPTION OF THE INVENTION

Figure 1:
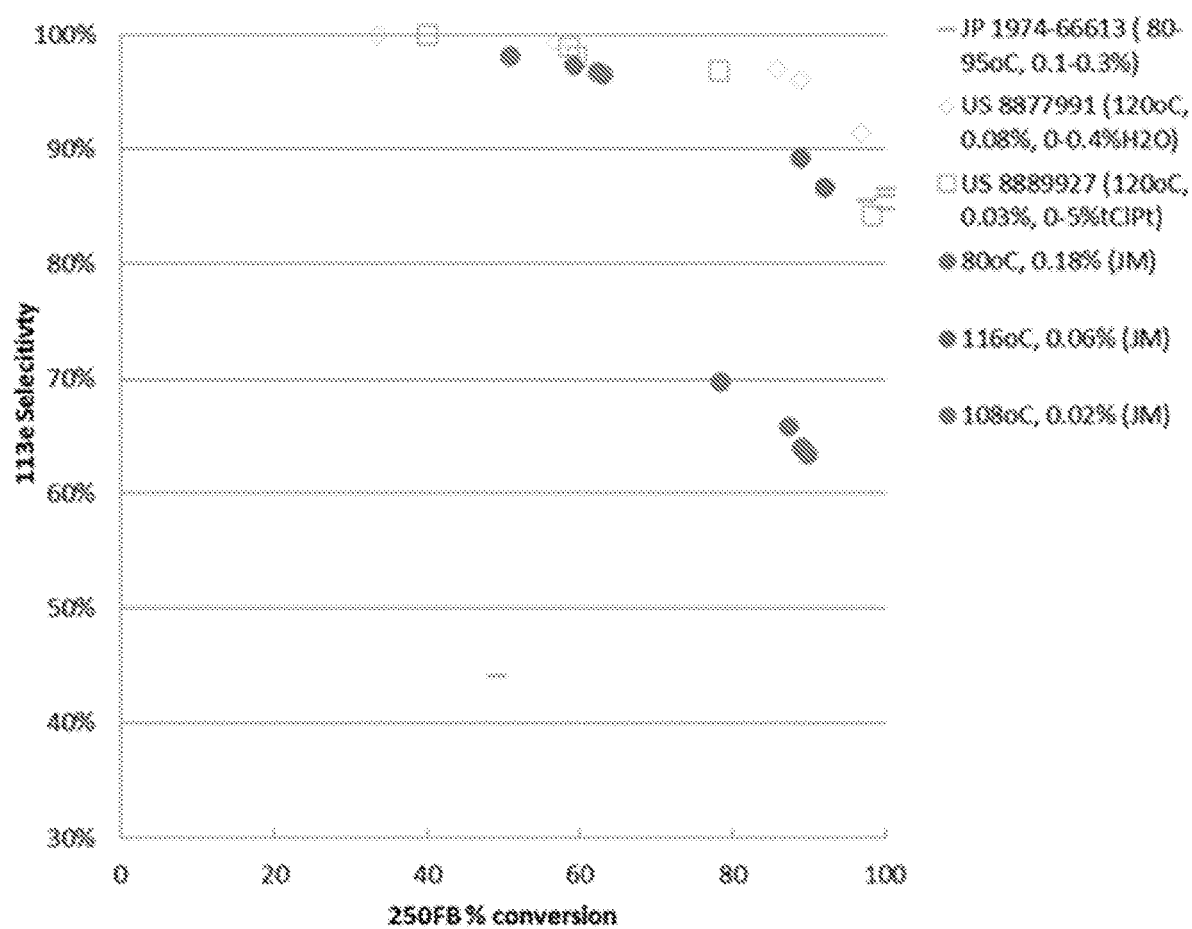
FIG. 1 is a graphical representation showing the % selectivity to 1,1,3-trichloropropene versus the % conversion of 1,1,1,3-tetrachloropropane.

Disclosed herein are processes for the preparation and isolation of halogenated alkenes. In general, the process comprises an anhydrous liquid phase reaction between at least one halogenated alkane and a homogeneous catalyst under conditions detailed below.

In all embodiments, an anhydrous liquid reaction mixture in a reactor is prepared by contacting at least one halogenated alkane and a homogeneous catalyst. The homogeneous catalyst comprises at least one metal salt and optionally at least one solvent. Once the anhydrous liquid reaction mixture is heated, the at least one chlorinated alkene, light by-products, and heavy by-products are formed. After separation of the at least one chlorinated alkene, the heavy by-products are disposed of.

Compared to other conventional processes, these processes have been shown to provide an improvement in yield, cycle time, selectivity, waste reduction, and lower manufacturing cost. In another aspect of the present invention, after removal of the at least one halogenated alkene, the unreacted or excess at least one chlorinated alkane and the optional solvent are recycled back into the process providing added efficiencies. In an additional aspect of the present invention, anhydrous HCl, a valuable by-product from the process, is captured and may be utilized in other processes or sold commercially.

(I) Processes for the Production of Halogenated Alkenes

One aspect of the present disclosure encompasses processes for the preparation of halogenated alkenes. The processes comprise: a) preparing an anhydrous liquid reaction mixture in a reactor comprising at least one halogenated alkane and at least one homogeneous catalyst wherein the at least one homogeneous catalyst comprises at least one metal salt, and optionally a solvent; b) heating the anhydrous liquid reaction mixture to form at least one halogenated alkene, light by-products, and heavy by-products; c) separating the at least one halogenated alkene from the anhydrous liquid reaction mixture; and d) disposing of the heavy by-products. By utilizing at least one homogenous catalyst, lower capital costs are realized and thus lower overall manufacturing cost.

(a) Anhydrous Liquid Phase Reaction Mixture

The process commences by preparing an anhydrous liquid phase reaction mixture. The anhydrous liquid phase reaction mixture comprises contacting at least one halogenated alkane and at least one homogeneous catalyst. The homogeneous catalyst is prepared by contacting at least one metal salt and optionally a solvent.

(i) At Least One Halogenated Alkane

A wide variety of halogenated alkanes may be used in the process. In one embodiment, the halogenated alkane may be a chlorinated alkane wherein the chlorinated alkane comprises between two to six carbon atoms and at least one chlorine atom where the chlorinated alkane comprising 3 carbon atoms and at least one chlorine atom is preferred. Non-limiting examples of chlorinated alkanes which may be used in the process may be a chlorinated ethane, a chlorinated propane, a chlorinated butane, a chlorinated pentane, a chlorinated hexane, or combinations thereof. Non-limiting examples of chlorinated alkanes may be ethyl chloride, 1,2-dichloroethane, 1,1,2,2-tetrachloroethane, pentachloroethane, 1,1-dichloropropane; 1,2-dichloropropane; 1,3-dichloropropane; 1,1,1-trichloropropane; 1,1,2-trichloropropane; 1,2,2-trichloropropane; 1,2,3-trichloropropane; 1,1,1,2-tetrachloropropane; 1,1,2,2-tetrachloropropane; 1,1,1,3-tetrachloropropane; 1,1,2,3-tetrachloropropane; 1,1,3,3-tetrachloropropane; 1,1,1,2,3-pentachloropropane; 1,1,1,2,2-pentachloropropane, 1,1,2,3,3-pentachloropropane; 1,1,2,2,3-pentachloropropane; 1,1,1,3,3-pentachloropropane; 1,1,1,3,3,3-hexachloropropane; 1,1,2,2,3,3-hexachloropropane; or combinations thereof. In a preferred embodiment, the chlorinated propane may be 1,1,1,3-tetrachloropropane, 1,1,1,2,3-pentachloropropane, 1,1,1,3,3-pentachloropropane, 1-chlorobutane, 2 chlorobutane, 1,2-dichlorobutane, 1,4-dichlorobutane, 1,1,2-dichlorobutane, 1,1,1-trichlorobutane, 1,2,3-trichlorobutane, 1,2,4-trichlorobutane, 1,1,1,3-tetrachlorobutane, 1,2,3,4-tetrachlorobutane, 2,2,3,3-tetrachlorobutane, 1,1,1,3,3-pentachlorobutane, 1,1,2,2,4-pentachlorobutane, 1,1,2,3,4-pentachlorobutane, 1,1,2,3,4,4-hexachlorobutane, 1,1,2,2,3,3-hexachlorobutane, 1,1,1,4,4,4-hexachlorobutane, 1-chloropentane, 2-chloropentane, 3-chloropentane, 1,1-dichloropentane, 2,3-dichloropentane, 3,3-dichloropentane, 1,5-dichloropentane, 1,2,3-trichloropentane, 1,2,5-trichloropentane 1,3,5-trichloropentane, 1,1,5-trichloropentane, 1,1,1,5-tetrachloropentane, 1,1,2,5-tetrachloropentane, 1,1,1,2-tetrachloropentane, 1,1,3,3-tetrachloropentane, 2,2,4,4-tetrachloropentane, 1,1,1,2,3,3-hexachloropentane, 1,1,1,3,3,5-hexachloropentane, 1,1,1,3,5,5-hexachloropentane, 1,1,1,3,3,4,4-heptachloropentane, 1,1,1,3,3,5,5-heptachloropentane, 1,1,1,3,3,5,5,5-octachloropentane, 1,1,1,2,2,3,3,4,5-nonachloropentane, 1-chlorohexane, 3-chlorohexane, 1,6-dichlorohexane, 1,1-dichlorohexane, 1,2-dichlorohexane, 1,2,6-trichlorohexane, 1,2,3-trichlorohexane, 1,1,1,2-tetrachlorohexane, 1,1,1,3-tetrachlorohexane, 1,2,5,6-tetrachlorohexane, 1,1,2,2-tetrachlorohexane, 1,2,3,4,5-pentachlorohexane, 1,1,1,3,6-pentachlorohexane, 1,2,4,4,6-pentachlorohexane, 1,1,1,3,6-pentachlorohexane, or combinations thereof. In a preferred embodiment, the halogenated alkane may be a chlorinated propane. Non-limiting examples of preferred chlorinated propanes may comprise 1,1,1,3-tetrachloropropane, also known as 250FB. 1,1,1,2,3-pentachloropropane, also known as 240DB, 1,1,1,3,3-pentachloropropane, also known as 240FA, or combinations thereof.

One method for preparing these chlorinated alkanes is through the telomerization process. In this process, carbon tetrachloride (Tet), an alkene or chlorinated alkene, a catalyst system comprising metallic iron, ferric chloride, and/or ferrous chloride, and a trialkylphosphate and/or a trialkylphosphite are contacted to produce the chlorinated alkanes. As an illustrative example, using ethylene as the monomer in the above described telomerization process yields tetrachloropropanes or pentachloropropanes. Utilizing vinyl chloride as the monomer, pentachloropropanes would result. The skilled artisan readily knows other methods for preparing chlorinated alkanes.

The halogenated alkane may be crude (unpurified product from the telomerization reaction), partially purified, or fully purified by means known to the skilled artisan. The crude or partially purified halogenated alkane may further comprise trialkylphosphate, a trialkylphosphite, iron hydroxide, light by-products, and heavy by-products.

(ii) At Least One Homogeneous Catalyst

A homogeneous catalyst may be used in the process. As used herein, the term "homogeneous catalyst" refers to a transition metal salt that is dissolved in at least one solvent. The homogeneous catalyst, as described herein, does not utilize a ligand (such as phosphates or phosphites, e.g., tributylphosphate) or a promoter (such as a free radical generator, e.g. AIBN). Non-limiting examples of metals salts may be an aluminum salt, a bismuth salt, a chromium salt, a cobalt salt, a copper salt, a gallium salt, a gold salt, an indium salt, an iron salt, a lead salt, a magnesium salt, a manganese salt, a mercury salt, a nickel salt, a platinum salt, a palladium salt, a rhodium salt, a samarium salt, a scandium salt, a silver salt, a titanium salt, a tin salt, a zinc salt, a zirconium salt, and combinations thereof. In a preferred embodiment, the transition metal salt may be an iron salt. Non-limiting examples of anions used in the suitable transition metal salts may include acetates, acetylacetonates, alkoxides, butyrates, carbonyls, dioxides, halides, hexanoates, hydrides, mesylates, octanoates, nitrates, nitrosyl halides, nitrosyl nitrates, sulfates, sulfides, sulfonates, phosphates, and combinations thereof. Non-limiting examples of suitable transition metal salts may iron (II) chloride, iron (III) chloride, iron (II) bromide, iron (II) iodide, iron (III) bromide, and iron (III) oxide. In a preferred embodiment, the transition metal salt may be iron (II) chloride, iron (III) chloride, or combinations thereof. In another preferred embodiment, the homogeneous iron catalyst comprises $FeCl_3$.

As appreciated by the skilled artisan, the homogeneous catalyst, once in the process, may undergo and oxidation and/or reduction to produce an activated catalytic species in various oxidation states. The oxidation state of these active iron catalytic species may vary, and may be for examples (I), (II), and (III). In one aspect, the active iron catalyst may in the Fe(I) oxidation state. In another aspect, the active iron catalyst may be Fe(II). In still another aspect, the active iron catalyst may be in the Fe(III) oxidation state. In an additional aspect, the active iron catalyst may comprise a mixture of Fe(I) and Fe(II). In still another aspect, the active iron catalyst may comprise a mixture of Fe(I) and Fe(III) oxidation states. In yet another aspect, the active iron catalyst may be in the Fe(II) and Fe(III) oxidation states. In another aspect, the active iron catalyst may in the Fe(I), Fe(II) and Fe(III) oxidation states. In still another embodiment, an electrochemical cell may be utilized to adjust the ratio of Fe(I), Fe(II), and Fe(III) in the process. The transition metal is essentially dry, i.e., it has a water content of the below 1000 ppm.

Generally, the concentration of the homogeneous catalyst in the reaction mixture may be less than 0.06 weight % (wt %) based on the total weight of the process. In various embodiments, the concentration of the homogeneous catalyst may be less than 0.06 wt %, less than 0.05 wt %, less than 0.04 wt %, less than 0.03 wt %, less than 0.02 wt %, less than 0.01 wt %, or less than 0.005 wt % based on the total weight of the components of the process.

(iii) Optional Anhydrous Solvent

An optional anhydrous solvent may be used in the process. The solvent, as defined herein, does not participate in the process. The optional anhydrous solvent may be non-polar or polar. Non-limiting examples of suitable solvents may be an aliphatic solvent, a halogenated aliphatic solvent, an aromatic solvent, a halogenated aromatic solvent, an ether solvent, an amide solvent, an alcohol solvent, a sulfoxide solvent, or combinations thereof. In an embodiment, the optional anhydrous solvent may be an alcohol solvent. Non-limiting examples of anhydrous alcohol solvent may be methanol, ethanol, n-propanol, 2-propanol, n-butanol, iso-butanol, or combinations thereof. In one embodiment, the solvent comprises methanol. In another embodiment, the anhydrous solvent is a halogenated alkane which is utilized in the process. The anhydrous solvent is essentially dry, i.e., it has a water content of the below 1000 ppm. In a preferred embodiment, the homogeneous catalyst is dissolved in anhydrous methanol prior to addition to the reactor. In another preferred embodiment, the homogeneous catalyst is dissolved in a halogenated alkane, such as 1,1,1,3-tetrachloropropane or 1,1,1,2,3-pentachloropropane. Anhydrous solvents typically have a water content of the below 2000 ppm or below 1000 ppm or below 500 ppm or below 250 ppm.

(b) Reaction Conditions

In general, the process for producing a chlorinated alkene includes carrying out the dehydrochlorination reaction at process conditions to enable the preparation of an effective high yield of the chlorinated alkene product.

The process commences by contacting the at least one chlorinated alkane (either purified, partially purified, or unpurified), at least one homogeneous catalyst, and optionally a solvent. The components of the process may be added in any order into the process.

The temperature of the process can and will vary depending on purity of the at least one chlorinated alkane, the homogeneous catalyst chosen, and the optional solvent chosen. Generally, the temperature of the process may be generally conducted at a temperature greater than 100° C. In various embodiments, the temperature of the process if greater than 100° C., greater than 110° C., greater than 120° C., greater than 130° C., greater than 140° C., or greater than 150° C.

The pressure of the process may be greater than 0 psig. In various embodiments, the pressure of the process may be greater than 0 psig, greater than 50 psig, greater than 100 psig, greater than 200 psig, greater than 1000 psig, or greater than 2000 psig. In a preferred embodiment, the pressure of the process may be adjusted to obtain a boiling bed (where the vapor pressure of the liquid mixture is the same as the reactor pressure that the liquid product starts to boil) condition. In an alternate embodiment, the pressure is less than 0 psig.

Generally, the reaction is allowed to proceed for a sufficient period of time until the reaction is complete, as determined by any method known to the skilled artisan, such as chromatography (e.g., GC). The duration of the reaction may range from about 5 minutes to about 12 hours. In some embodiments, the duration of the reaction may range from about 5 minutes to about 10 hours, from about 30 minutes to about 9 hours, from about 1 hours to about 8 hours, or from about 4 hours to about 7 hours.

As appreciated by the skilled artisan, the above process may be run in a batch mode or a continuous mode where continuous mode is preferred. In another embodiment, the process in continuous modes may be stirred in various methods as appreciated by the skilled artisan.

The chlorinated alkane fed to the above described process may be converted to the chlorinated alkene isomers in at least 60% conversion. In various embodiments, the conversion of chlorinated alkane to the chlorinated alkene isomers may be at least 60%, at least 70%, at least 75%, at least 85%, at least 95%, and at least 99%.

(II) Separation and Recycle Product Effluent Streams for the Process

The next step in the process comprises separating purified halogenated alkenes from the anhydrous liquid reaction mixture comprising the halogenated alkene, homogeneous catalyst, an optional solvent, lighter by-products, heavier by-products, and unreacted chlorinated alkane starting material as product effluent streams. Depending on the purity of the halogenated alkane used in the process, further components in the anhydrous liquid phase reaction mixture may be a trialkylphosphate, a trialkylphosphite, and iron hydroxide.

The separation process commences by transferring a portion of the anhydrous liquid phase reaction mixture into a separator or multiple separators. In various embodiments, the at least one of the first separator and the second separator may a distillation column or a multistage distillation column. Additionally, the at least one of the first separator and the second separator may further comprise a reboiler, a bottom stage, or a combination thereof. Various distillation columns may be used in this capacity. In one embodiment, a side draw column or a distillation column which provides outlet stream from an intermediate stage or a divided wall column (dividing wall column (DWC) is a single shell, fully thermally coupled distillation column capable of separating mixtures of three or more components into high purity products (product effluent streams) may be used as a separator. A portion of various product effluent streams after separation or a portion of the anhydrous liquid reaction mixture produced by the process may be optionally recycled back into the reactor to provide increased kinetics, increased efficiencies, reduced overall cost of the process, increased selectivity of the desired halogenated alkane, increased yield of the desired halogenated alkane, and increased mixing.

As appreciated by the skilled artisan, each product effluent stream, as described below, is enriched in the particular component of the anhydrous liquid phase reaction mixture. Further separation may be required of each product effluent streams to produce highly pure compounds.

In another embodiment, the process may be conducted in a reactive distillation column. In this configuration, the chemical reactor and the distillation are combined in a single operating step. Thus, allowing for simultaneous addition of reactants into the process, addition of various product streams, and distillation of various product effluent streams from the process.

A portion of the anhydrous liquid reaction is then transferred into a separator. In an embodiment, the separator may utilize at least one simple distillation, at least one vacuum distillation, at least one fractional distillation, or combinations thereof. The distillations may comprise at least one theoretical plate.

As appreciated by the skilled artisan, separating the purified halogenated alkene from the anhydrous liquid reaction mixture would produce at least two product effluent streams. In various embodiments, separating the purified halogenated alkene may produce three product effluent streams, four product effluent streams, or more product streams depending on the separation device utilized. As an example, the separation of the halogenated alkene from the contents of the reactor using three product streams is shown below.

The anhydrous liquid reaction mixture may be distilled to produce three product streams, product effluent streams (a), (b), and (c). Product effluent stream (a) comprises the optional solvent, light by-products, and anhydrous hydrogen halide which under the process conditions described above is removed as a gas as an overhead stream during the separation. Product effluent stream (b) comprises the halogenated alkene which may be removed as a side stream. Product (c) comprises unreacted halogenated alkane, heavy by-products, and the at least one homogeneous catalyst which comprises the bottom stream.

Generally, product effluent streams (a) comprising the optional solvent, anhydrous hydrogen halide, and light by-products may be further purified producing two additional product effluent streams (d) and (e) wherein product effluent stream (d) obtained as an overhead stream comprises anhydrous hydrogen halide, light by-products and product effluent stream (e), obtained as the bottom stream, comprising the optional solvent. The overhead product effluent stream (d) may be further purified since anhydrous hydrogen halide, such as HCl, is a valuable commercial material.

Product effluent stream (c) may be further purified producing two additional product effluent streams (f) and (g) wherein product effluent stream (f) comprises the unreacted halogenated alkane and product effluent stream (g) comprises heavy by-products and the homogeneous catalyst.

In order to improve the efficiency of the process, various product effluent streams may be externally recycled back into the process. In various embodiments, at least a portion of the product effluent stream (a) comprising optional solvent, light by-products, and anhydrous hydrogen halide, product effluent stream (e) comprising the optional solvent, and product stream (g) comprising unreacted halogenated alkane may be recycled back into the dehydrochlorination process, as described above.

In another embodiment, at least a portion of product effluent stream (e) and/or (g) may be mixed with fresh liquid feed (comprising non-recycled halogenated alkane and optional solvent) before being recycled back into the reactor in batch mode or continuous mode. In various embodiments, the product effluent streams and fresh liquid feeds may be introduced into the reactor separately or mixed together before entering the process. To be clear, fresh feed streams may contain all or less than all of the following: the halogenated alkane and the optional solvent. The introduction of these fresh liquid feeds into the reactor or mixing the recycle streams with fresh liquid feeds increases the efficiency of the process, reduces the overall cost, maintains the kinetics, maintains the reaction conversion, increase the through-put, and reduces the by-products produced by the process. The amounts of the product effluent streams recycled to the reactor or fresh liquid feeds added to the reactor may be the same or different. One way to measure the amount of product effluent streams and/or fresh liquid feeds being added to the reactor is to identify the mass flow of the materials. The product effluent stream being recycled to the reactor has a product effluent stream mass flow, while the fresh liquid feeds being added to the reactor has a fresh liquid feed mass flow. Mass flows may be measured using methods known in the art.

Generally, the mass of the product effluent stream mass flow being recycled to the fresh liquid feed mass flow is adjusted to not only maintain the conversion of the process but also maintain the kinetics of the process.

Product effluent stream (b) from the separator comprising the halogenated alkene produced in the dehydrohalogenation process may have a yield of at least about 10%. In various embodiments, product effluent stream (b) comprising chlorinated alkene produced in the process may have a yield of at least about 20%, at least about 50%, at least about 70%, at least about 75%, at least about 80%, at least about 85%, at least about 90%, at least about 95%, or at least about 99%.

In an alternate embodiment, the lights are removed and if desired, further distilled to afford separated components. For example, anhydrous HCl may be isolated from the lights. Then the at least a portion of the remaining liquid reaction mixture is sent to a distillation column, where the alkene can be separated from the starting material and the heavies. The heavies may be purified and recycled to the reactor, the heavies may be distilled and only the catalyst can be recycled, while the residual heavies are discarded or all of the heavies can be discarded.

(III) Preferred Embodiment: Process for Preparing of 1,1,3-Trichloropropene, 3,3,3-Trichloropropene, or Combinations Thereof

(a) Process for Preparing 1,1,3-trichloropropane, 3,3,3-trichloropropane, or Combinations Thereof Another aspect of the present disclosure encompasses process for preparing 1,1,3-trichloropropene; 3,3,3-trichloropropene, or combinations thereof. The process commences by preparing and reacting a mixture comprising 1,1,1,3-tetrachloropropane; a homogeneous catalyst, and an optional solvent. The homogeneous catalyst is described above in Section (I)(a)(ii) and the optional solvent is described above in Section (I)(a)(iii). In a preferred embodiment, the homogeneous catalyst comprises $FeCl_3$ and the optional solvent comprises anhydrous methanol, 1,1,1,3-tetrachloropropane, or combinations thereof.

(b) Reaction Conditions

The reaction conditions are described above in Section (I)(b).

(c) Output from the Process to Prepare 1,1,3-trichloropropene, 3,3,3-trichloropropene, or Combinations Thereof The 1,1,1,3-tetrachloropropane fed to the above described process may be converted to 1,1,3-trichloropropene, 3,3,3-trichloropropene, or combinations thereof in at least 60% conversion. In various embodiments, the conversion of 1,1,1,3-tetrachloropropane to 1,1,3-trichloropropene; 3,3,3-trichloropropene or combinations thereof may be at least 60%, at least 70%, at least 75%, at least 85%, at least 95%, and at least 99%.

The selectivity to 1,1,3-trichloropropene; 3,3,3-trichloropropene or combinations thereof can and will vary depending on the reaction conditions, the purity level of the 1,1,1,3-tetrachloropropane utilized, and the 1,1,3-trichloropropene; 3,3,3-trichloropropene, or combinations thereof produced. Generally, the selectivity to 1,1,3-trichloropropene; 3,3,3-trichloropropene, or combinations thereof may be greater than 70%. In various embodiments, the selectivity to the 1,1,3-trichloropropene; 3,3,3-trichloropropene, or combinations thereof may be greater than 70%, greater than 80%, greater than 90%, or greater than 95%. In preferred embodiments, the selectivity to the 1,1,3-trichloropropene; 3,3,3-trichloropropene or combinations thereof may range from 95% to 99%.

(d) Separation of the 1,1,3-trichloropropene, 3,3,3-trichloropropene, or Combinations Thereof and Recycling Product Effluent Streams The process for separating the 1,1,3-trichloropropene; 3,3,3-trichloropropene, or combinations thereof from the reactor contents is described above in Section (II). Specific recycle streams useful in improving the efficiency of the process are described above in Section (II).

The product effluent stream (b) from the separator comprising the 1,1,3-trichloropropene; 3,3,3-trichloropropene, or combinations thereof produced in the dehydrochlorination process may have a yield of at least about 10%. In various embodiments, product effluent stream (b) comprising 1,1,3-trichloropropene; 3,3,3-trichloropropene, or combinations thereof produced in the process may have a yield of at least about 20%, at least about 50%, at least about 70%, at least about 75%, at least about 80%, at least about 85%, at least about 90%, at least about 95%, or at least about 99%.

(IV) Preferred Embodiment: Process for Preparing of 1,1,2,3-Tetrachloropropene, 2,3,3,3-Tetrachloropropene, or Combinations Thereof

(a) Process for Preparing 1,1,2,3-tetrachloropropene, 2,3,3,3-tetrachloropropene, or Combinations Thereof Another aspect of the present disclosure encompasses process for preparing 1,1,2,3-tetrachloropropene, 2,3,3,3-tetrachloropropene, or combinations thereof. The process commences by preparing and reacting a mixture comprising 1,1,1,2,3-pentachloropropane (240DB); a homogeneous catalyst, and an optional solvent. The homogeneous catalyst is described above in Section (I)(a)(ii) and the optional solvent is described above in Section (I)(a)(iii). In a preferred embodiment, the homogeneous catalyst comprises $FeCl_3$ and the optional solvent comprises anhydrous methanol, 1,1,1,2,3-pentachloropropane, or combinations thereof.

(b) Reaction Conditions

The reaction conditions are described above in Section (I)(b).

(c) Output from the Process to Prepare 1,1,2,3-tetrachloropropene, 2,3,3,3-tetrachloropropene, or Combinations Thereof The 1,1,1,2,3-pentachloropropane fed to the above described process may be converted to 1,1,2,3-tetrachloropropene, 2,3,3,3-tetrachloropropene, or combinations thereof in at least 60% conversion. In various embodiments, the conversion of 1,1,1,2,3-pentachloropropane to 1,1,2,3-tetrachloropropene, 2,3,3,3-tetrachloropropene, or combinations thereof may be at least 60%, at least 70%, at least 75%, at least 85%, at least 95%, and at least 99%.

The selectivity to 1,1,2,3-tetrachloropropene, 2,3,3,3-tetrachloropropene, or combinations thereof can and will vary depending on the reaction conditions, the purity level of the 1,1,1,2,3-pentachloropropane, and the 1,1,2,3-tetrachloropropene, 2,3,3,3-tetrachloropropene, or combinations thereof produced. Generally, the selectivity to 1,1,2,3-tetrachloropropene, 2,3,3,3-tetrachloropropene, or combinations thereof may be greater than 70%. In various embodiments, the selectivity to the 1,1,2,3-tetrachloropropene, 2,3,3,3-tetrachloropropene, or combinations thereof may be greater than 70%, greater than 80%, greater than 90%, or greater than 95%.

(d) Separation of the 1,1,2,3-tetrachloropropene, 2,3,3,3-tetrachloropropene, or Combinations Thereof and Recycling Product Effluent Streams The process for separating the 1,1,2,3-tetrachloropropene, 2,3,3,3-tetrachloropropene, or combinations thereof from the reactor contents is described above in Section (II). Specific recycle streams useful in improving the efficiency of the process are described above in Section (II).

The product effluent stream (b) from the separator comprising the 1,1,2,3-tetrachloropropene, 2,3,3,3-tetrachloropropene, or combinations thereof produced in the dehydrochlorination process may have a yield of at least about 10%. In various embodiments, the product effluent stream (b) comprising 1,1,2,3-tetrachloropropene, 2,3,3,3-tetrachloropropene, or combinations thereof produced in the process may have a yield of at least about 20%, at least about 50%, at least about 70%, at least about 75%, at least about 80%, at least about 85%, at least about 90%, at least about 95%, or at least about 99%.

(V) Preferred Embodiment: Process for Preparing of 1,1,3,3-Tetrachloropropene, 1,3,3,3-Tetrachloropropene, or Combinations Thereof (a) Process for Preparing 1,1,3,3-tetrachloropropene, 1,3,3,3-tetrachloropropene, or Combinations Thereof Another aspect of the present disclosure encompasses process for preparing 1,1,3,3-tetrachloropropene, 1,3,3,3-tetrachloropropene, or combinations thereof. The process commences by preparing and reacting a mixture comprising 1,1,1,3,3-pentachloropropane (240FA); a homogeneous catalyst, and an optional solvent. The homogeneous catalyst is described above in Section (I)(a)(ii) and the optional solvent is described above in Section (I)(a)(iii). In a preferred embodiment, the homogeneous catalyst comprises $FeCl_3$ and the optional solvent comprises anhydrous methanol, 1,1,1,3,3-pentachloropropane, or combinations thereof.

(b) Reaction Conditions

The reaction conditions are described above in Section (I)(b).

(c) Output from the Process to Prepare 1,1,3,3-tetrachloropropene, 1,3,3,3-tetrachloropropene, or Combinations Thereof The 1,1,1,3,3-pentachloropropane fed to the above described process may be converted to 1,1,3,3-tetrachloropropene, 1,3,3,3-tetrachloropropene, or combinations thereof in at least 60% conversion. In various embodiments, the conversion of 1,1,1,3,3-pentachloropropane to 1,1,3,3-tetrachloropropene, 1,3,3,3-tetrachloropropene, or combinations thereof may be at least 60%, at least 70%, at least 75%, at least 85%, at least 95%, and at least 99%.

The selectivity to 1,1,3,3-tetrachloropropene, 1,3,3,3-tetrachloropropene, or combinations thereof can and will vary depending on the reaction conditions, the purity level of the 1,1,1,3,3-pentachloropropane, and the 1,1,3,3-tetrachloropropene, 1,3,3,3-tetrachloropropene, or combinations thereof produced. Generally, the selectivity to 1,1,3,3-tetrachloropropene, 1,3,3,3-tetrachloropropene, or combinations thereof may be greater than 70%. In various embodiments, the selectivity to the 1,1,3,3-tetrachloropropene, 1,3,3,3-tetrachloropropene, or combinations thereof may be greater than 70%, greater than 80%, greater than 90%, or greater than 95%. In preferred embodiments, the selectivity to the 1,1,3,3-tetrachloropropene, 1,3,3,3-tetrachloropropene, or combinations thereof may range from 95% to 99%.

(d) Separation of the 1,1,3,3-tetrachloropropene, 1,3,3,3-tetrachloropropene, or Combinations Thereof and Recycling Product Effluent Streams The process for separating the 1,1,3,3-tetrachloropropene, 1,3,3,3-tetrachloropropene, or combinations thereof from the reactor contents is described above in Section (II). Specific recycle streams useful in improving the efficiency of the process are described above in Section (II).

The first product stream from the separator comprising the 1,1,3,3-tetrachloropropene, 1,3,3,3-tetrachloropropene, or combinations thereof produced in the dehydrochlorination process may have a yield of at least about 10%. In various embodiments, the first product stream comprising 1,1,3,3-tetrachloropropene, 1,3,3,3-tetrachloropropene, or combinations thereof produced in the process may have a yield of at least about 20%, at least about 50%, at least about 70%, at least about 75%, at least about 80%, at least about 85%, at least about 90%, at least about 95%, or at least about 99%.

(VI) Further Reaction of the Chlorinated Alkenes

In one aspect, disclosed herein are processes for the conversion of halogenated alkenes, such as 1,1,3-trichloropropene, 3,3,3-trichloropropene, or combinations thereof; 1,1,2,3-tetrachloropropene, 2,3,3,3-tetrachloropropene, or combinations thereof; and 1,1,3,3-tetrachloropropene, 1,3,3,3-tetrachloropropene, or combinations thereof, to one or more hydrofluoroolefins. These processes comprise contacting the halogenated alkenes with a fluorinating agent in the presence of a fluorination catalyst, in a single reaction or two or more reactions. These processes can be conducted in either gas phase or liquid phase with the gas phase being preferred at temperatures ranging from 50° C. to 400° C.

Generally, a wide variety of fluorinating agents can be used. Non-limiting examples of fluorinating agents include HF, $F_2$, ClF, $AlF_3$, KF, NaF, $SbF_3$, $SbF_5$, $SF_4$, or combinations thereof. The skilled artisan can readily determine the appropriate fluorination agent and catalyst. Examples of hydrofluoroolefins that may be produced utilizing these processes include, but are not limited to 2,3,3,3-tetrafluoroprop-1-ene (HFO-1234yf), 1,3,3,3-tetrafluoroprop-1-ene (HFO-1234ze), 3,3,3-trifluoroprop-1-ene (HFO-1243zf), and 1-chloro-3,3,3-trifluoroprop-1-ene (HFCO-1233zd).

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "1113" refers to 1,1,3-trichloropropene.
The term "333" refers to 3,3,3-trichloropropene.
The term "1123" refers to 1,1,2,3-tetrachloropropene.
The term "2333" refers to 2,3,3,3-tetrachloropropene.
The term "1133" refers to 1,1,3,3-tetrachloropropene.
The term "1333" refers to 1,3,3,3-tetrachloropropene.
The term "250FB" refers to 1,1,1,3-tetrachloropropane.
The term "240DB" refers to 1,1,1,2,3-pentachloropropane.
The term "240FA" refers to 1,1,1,3,3-pentachloropropane.

Having described the invention in detail, it will be apparent that modifications and variations are possible without departing from the scope of the invention defined in the appended claims.

EXAMPLES

The following examples illustrate various embodiments of the invention.

Example 1: Preparation of 1,1,3-trichloropropene, 3,3,3-trichloropropene, or Combinations Thereof from 1,1,1,3-tetrachloropropane In a 500 mL 3-neck round bottom flask equipped with a condenser was placed 250 mL of 1,1,1,3-tetrachloropropane (250FB) and the FeCl$_3$ catalyst. The flask was heated by an external heating mantle and stirred to maintain the desired temperature of the process to ensure fluidization and mixing of the FeCl$_3$ catalyst. The condenser was maintained at room temperature to allow for the HCl and light by-products to escape the process while condensing the product and reactant back to the flask. A sample was drawn every 30 minutes from the reaction mixture to determine the yield and conversion.

FIG. 1 shows the significant selectivity improvement of using <0.06 wt % FeCl$_3$ and temperature above 100° C. at conversion above 60% as compared to higher wt % FeCl$_3$ and lower temperature. This example demonstrates that this preferred condition can performed as well as other reported in the literature without using H$_2$O (U.S. Pat. No. 8,877,991) or heavies containing tetrachloropentane (U.S. Pat. No. 8,889,927).

Example 2: Preparation of 1,1,3-trichloropropene, 3,3,3-trichloropropene, or Combinations Thereof from 1,1,1,3-tetrachloropropane Using Reactive Distillation The experiment was set up in a similar way as described in example 1 except the temperature was raised to achieve boiling of the product.

Figure 2:
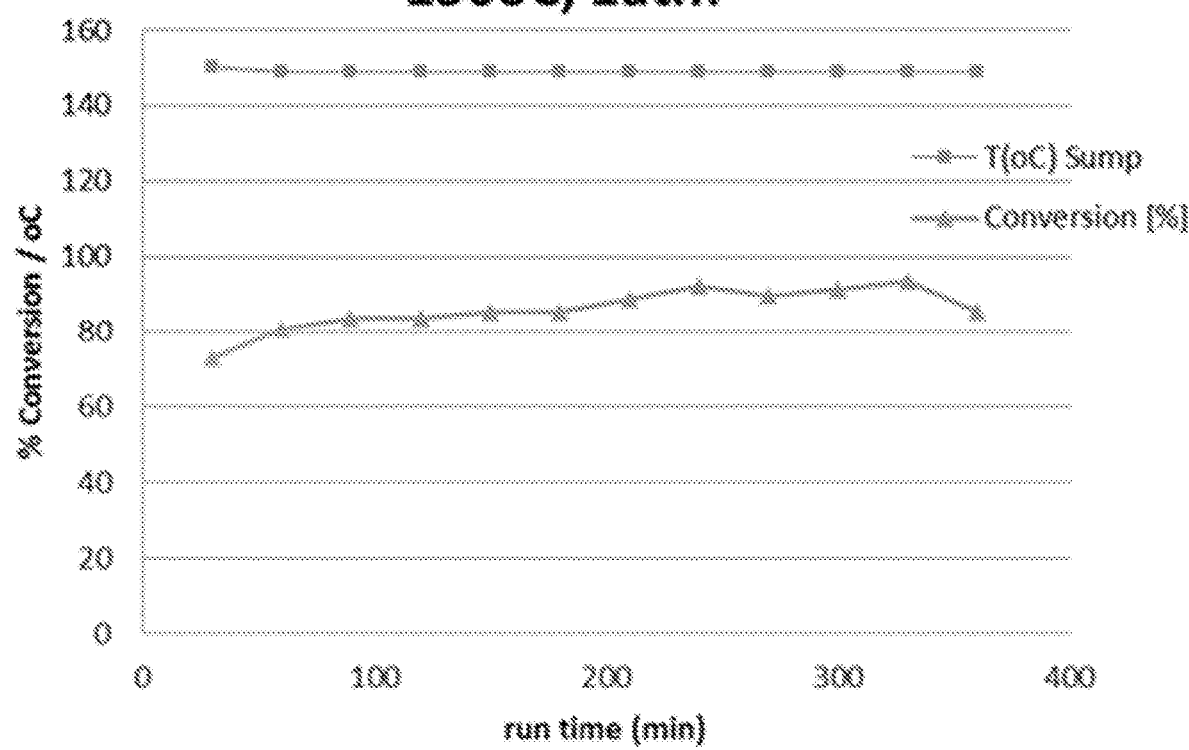
FIG. 2 is a graphical representation showing the % conversion of 1,1,1,3-tetrachloropropane versus run time in a continuous stirred reactor maintained at 150° C. and 1 atmosphere.

FIG. 2 shows a continuous reactive distillation of 250FB conversion to 113e at about 150° C. and at ambient pressure with dissolved FeCl$_3$ of about 8 ppm by weight. The reactor was heated using glycerol bath at 170° C. and stirred. The selectivity of 113e was found to be >99%. A total of about 110 gr of 113e was recovered at the end of the run.

What is claimed is:

1. A process for preparing halogenated alkenes, the process comprising:
   a) preparing a liquid reaction mixture, wherein the reaction mixture comprises at least one halogenated alkane and at least one homogeneous catalyst comprising at least one metal salt, wherein the concentration of the homogeneous catalyst in the reaction mixture is 50 ppm or less; and
   b) forming, from a reaction of the reaction mixture, at least one halogenated alkene, wherein the reaction is carried out at a temperature of at least 150° C.

2. The process of claim 1, wherein the concentration of the homogeneous catalyst in the reaction mixture is 8 ppm or less.

3. The process of claim 1, wherein the concentration of the homogeneous catalyst in the reaction mixture is 8 ppm to 50 ppm.

4. The process of claim 1, wherein the concentration of the homogeneous catalyst in the reaction mixture is 10 ppm or less.

5. The process of claim 4, wherein the homogeneous catalyst comprises one or more of FeCl$_3$ or GaCl$_3$.

6. The process of claim 4, wherein the homogeneous catalyst comprises FeCl$_3$.

7. The process of claim 1, wherein the concentration of the homogeneous catalyst in the reaction mixture is 30 ppm or less.

8. The process of claim 1, wherein the at least one metal salt is selected from the group of an aluminum salt, a bismuth salt, a chromium salt, a cobalt salt, a copper salt, a gallium salt, a gold salt, an indium salt, an iron salt, a lead salt, a magnesium salt, a manganese salt, a mercury salt, a nickel salt, a platinum salt, a palladium salt, a rhodium salt, a samarium salt, a scandium salt, a silver salt, a titanium salt, a tin salt, a zinc salt, a zirconium salt, and combinations thereof.

9. The process of claim 1, wherein the reaction is carried out at a pressure of at least 0 psig.

10. The process of claim 1, wherein the conversion of the at least one halogenated alkane is greater than 50%.

11. The process of claim 1, wherein the conversion of the at least one halogenated alkane is greater than 70%.

12. The process of claim 1, wherein the selectivity to the at least one halogenated alkene is greater than 90%.

13. The process of claim 1, wherein the selectivity to the at least one halogenated alkene is greater than 99%.

14. The process of claim 1, wherein the halogenated alkane is a chlorinated alkane.

15. The process of claim 12, wherein the chlorinated alkane is one or more members selected from the group of 1,1,1,3-tetrachloropropane (250FB), 1,1,1,2,3-pentachloropropane (240DB), 1,1,1,3,3-pentachloropropane (240FA).

16. The process of claim 1, wherein the halogenated alkene is a chlorinated alkene.

17. The process of claim 16, wherein the chlorinated alkene comprises between 2 and 6 carbon atoms and one less chlorine atom as compared to the chlorinated alkane.

18. The process of claim 16, wherein the chlorinated alkene is a chlorinated propene.

19. The process of claim 1, wherein the liquid reaction is anhydrous.

20. The process of claim 1, wherein preparing the liquid reaction mixture comprises adding the homogeneous catalyst dissolved in a solvent.

* * * * *